United States Patent [19]

de Wied et al.

[11] 4,271,152
[45] Jun. 2, 1981

[54] PSYCHO-PHARMACOLOGICAL PEPTIDES

[75] Inventors: David de Wied, Biethoven; Hendrik M. Greven, Heesch, both of Netherlands

[73] Assignee: Akzo N.V., Arnhem, Netherlands

[21] Appl. No.: 123,060

[22] Filed: Feb. 20, 1980

[30] Foreign Application Priority Data

Feb. 21, 1979 [NL] Netherlands ............... 7901348

[51] Int. Cl.³ .................. A61K 37/00; C07C 103/52
[52] U.S. Cl. ........................... 424/177; 260/112.5 R
[58] Field of Search ................. 260/112.5 R; 424/177

[56] References Cited

U.S. PATENT DOCUMENTS 4,203,975  5/1980  Greven ..................... 260/112.5 R Primary Examiner—Delbert R. Phillips
Attorney, Agent, or Firm—Haseltine and Lake

[57] ABSTRACT

The present invention relates to novel psycho-pharmacological active peptides and peptide derivatives of the formula:

A-R-L-Ser-R₁-L-Thr-L-Pro-L-Leu-L-Val-L-Thr-B wherein
R represents the amino acid residue L-Lys or L-Arg,
R₁ represents the amino acid residue L-Glu or L-Gln,
B represents one of the following amino acid or peptide-radicals:
L-Leu-OH, (α-dehydro)Leu-OH
D-Leu-OH
L-Leu-L-Phe-OH
L-Leu-L-Phe-L-Lys-OH
L-MeLeu-OH or the radical

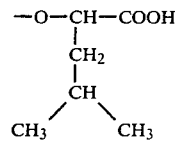

and A represents one of the following radicals or residues:
hydrogen
H-L-Glu
$Z_1$-L-Glu
$Z_2$-L-Ser-L-Glu-
H-$Q_1$-L-Thr-L-Ser-L-Glu-
$Q_2$-L-Thr-L-Ser-L-Glu-
$Z_3$-$Q_1$-L-Thr-L-Ser-L-Glu- or
$H_2N$-ALK-CO-L-Phe-$Q_1$-L-Thr-L-Ser-L-Glu-
in which
$Z_1$ represents H-L-Ser, H-D-Ser, desamino-Ser, 2,3-dihydroxy propanoyl or $H_2N$-ALK-CO-,
$Z_2$ represents H-L-Thr, H-D-Thr, desamino-Thr, 2,3-dihydroxybutanoyl or $H_2N$-ALK-CO;
$Q_1$ represents L-Met, L-Met(O), L-Met (O₂) or L-Leu
$Q_2$ represents H-D-Met, H-D-Met (O), H-D-Leu, H-D-Met (O₂), desamino Met, desamino Met (O), desamino Leu, desamino Met (O₂), 2-hydroxy-4-methylthiobutanoyl, 2-hydroxy-4-methylpentanoyl or the radical $H_2N$-ALK-CO,
$Z_3$ represents H-L-Phe, H-D-Phe, desamino Phe, 2-hydroxy-3-phenyl-propanoyl and $H_2N$-ALK-CO-,
and
ALK represents an alkylene or alkylidene group with 1–6 carbon atoms,
as well as the functional derivatives thereof.

10 Claims, No Drawings

PSYCHO-PHARMACOLOGICAL PEPTIDES

The present invention relates to novel psycho-pharmacologically active peptides and peptide derivatives derived from a certain fragment of the hormone β-lipotropin (β-LPH). β-Lipotropin is a polypeptide, consisting of 91 amino-acids, being formed in the posterior lobe of the hypophysis, and shows fat mobilising activity.

A few β-LPH fragments are already known and described in literature. It is known, for example, that the fragment γ-lipotropin (β-LPH-(1-58)) just as β-LPH itself has fat mobilising properties. The fragment β-LPH-(41-58), called β-melanotropin, is capable of influencing the pigmentation of the skin by stimulating the melanocytes. It is further, known that the sequence of β-LPH-(61-91)(β-endorphin) has an analgetic effect, which can be antagonized by naloxon, just as in case of morphine, so that the supposition of both morphine and β-endorphin affecting the same receptor is self-evident.

In the meantime it is also known for small peptide fragments of β-endorphin to have an affinity to the opiate receptor, for example, β-LPH-(61-76)(called α-endorphin), the fragment β-LPH-(61-69) and the fragment β-LPH-(61-65)) (called Met-enkephalin). See Nature 258, 577 (1975).

An affinity to the opiate receptor has also been described for the endogenous peptide Leu-enkephaline [Leu$^{65}$]β-LPH-(61-65), and for the synthetic D-Ala$^2$-Met-enkephalin, [D-Ala$^{62}$]β-LPH-(61-65). See e.g. Science 194, 330 (1976).

It has furthermore already been ascertained that β-endorphin (β-LPH-(61-91)) has certain psycho-pharmacological properties. For example, this peptide inhibits the extinction of the (active) flight behaviour of rats in the well-known pole-jumping test (pole-jumping avoidance behaviour).

This property of β-endorphin cannot be counteracted by known morphine antagonists such as naloxon or naltrexon, so that the conclusion that the psycho-pharmacological activity of β-endorphin is realised quite independently of the opiate receptor sides in the brains, is fully justified.

Apart from β-endorphin the smaller peptide fragments α-endorphin, the fragment β-LPH-(61-69) and Met-enkephalin derived therefrom have also been found to inhibit the extinction of the avoidance behaviour in a similar way.

Also the peptide γ-endorphin (β-LPH-(61-77)), which only differs from α-endorphin by the presence of only one additional amino-acid (leucine) on the C-terminal side, appeared to have psycho-pharmacological activity, be it of a completely different nature than that of the α- and β-endorphin. While α-endorphin delayed the extinction of the avoidance behaviour, γ-endorphin was shown, in contrast, to accelerate the extinction of the avoidance behaviour. It is remarkable that the addition of one amino-acid residue to the C-terminal part of α-endorphin gives rise to such a dramatic reversal of the behavioural activity.

The Dutch Patent Application No. 78.02289 (not pre-published) discloses that peptides with an amino-acid sequence β-LPH-(62-77) or closely related analogues derived therefrom accelerate the extinction of the avoidance behaviour to a greater extent than in case of γ-endorphin. Moreover, in contrast to γ-endorphin, said peptides have no longer a strong affinity to the opiate receptors.

Surprisingly it was found that the entire peptide sequence 62-77 of β-LPH was not necessary for the maintenance of said avoidance behaviour (acceleration of the extinction).

The present invention is therefor dealing with peptides which have one up to seven amino acid residues less than the peptides disclosed in the said Dutch patent application.

The new peptides of the invention have the general formula:

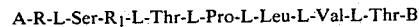

wherein
R represents the amino acid residue L-Lys or L-Arg,
R$_1$ represents the amino acid residue L-Glu or L-Gln,
B represents one of the following amino acid or peptide-radicals:
L-Leu-OH, (α-dehydro)Leu-OH
D-Leu-OH
L-Leu-L-Phe-OH
L-Leu-L-Phe-L-Lys-OH
L-MeLeu-OH
or the radical

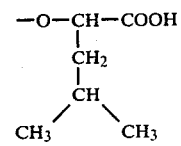

and A represents one of the following radicals or residues:
hydrogen
H-L-Glu
Z$_1$-L-Glu
Z$_2$-L-Ser-L-Glu-
H-Q$_1$-L-Thr-L-Ser-L-Glu-
Q$_2$-L-Thr-L-Ser-L-Glu-
Z$_3$-Q$_1$-L-Thr-L-Ser-L-Glu- or
H$_2$N-ALK-CO-L-Phe-Q$_1$-L-Thr-L-Ser-L-Glu-
in which
Z$_1$ represents H-L-Ser, H-D-Ser, desamino-Ser, 2,3-dihydroxy propanoyl or H$_2$N-ALK-CO-,
Z$_2$ represents H-L-Thr, H-D-Thr, desamino-Thr, 2,3-dihydroxybutanoyl or H$_2$N-ALK-CO;
Q$_1$ represents L-Met, L-Met(O), L-Met(O$_2$) or L-Leu
Q$_2$ represents H-D-Met, H-D-Met(O), H-D-Leu, H-D-Met(O$_2$), desamino Met, desamino Met(O), desamino Met(O$_2$), desamino Leu, 2-hydroxy-4-methylthiobutanoyl, 2-hydroxy-4-methylpentanoyl or the radical H$_2$N-ALK-CO,
Z$_3$ represents H-L-Phe, H-D-Phe, desamino Phe, 2-hydroxy-3-phenyl-propanoyl and H$_2$N-ALK-CO-,
and
ALK represents an alkylene or alkylidene group with 1-6 carbon atoms,
as well as the functional derivatives thereof.

More particularly the invention relates to a pharmaceutical composition comprising one or more of the peptides of formula I as the active constituent.

The peptides and peptide derivatives according to the general formula I are prepared in steps each of which are known to those in the art. The methods which are most frequently used for the preparation of the compounds herein referred to may be summarized as follows in three alternative processes:

(a) condensation in the presence of a condensing agent of (1) an amino-acid or peptide containing a free carboxyl group (and in which other reactive groups have been protected) with (2) a compound (amino-acid, peptide or amine) containing a free amino group (and in which other reactive groups have likewise been protected); or (b) condensation of (1) an amino-acid or peptide containing an activated carboxyl group, and in which other reactive groups have optionally been protected, with (2) a compound (amino-acid, peptide or amine) containing a free $NH_2$ group and in which other reactive groups have optionally been protected, or (c) condensation of (1) an amino-acid or peptide containing a free carboxyl group (and in which other reactive groups have been protected) with (2) a compound (amino-acid, peptide or amine) containing an activated amino group (and in which other reactive groups have optionally been protected); after which the protecting groups, if desired, are removed.

Methods of activating the carboxyl group are known to those skilled in the art, and include conversion of same into an acid halide, an azide, anhydride, imidazolide, or an activated ester such as the N-hydroxysuccinimide ester or the p-nitrophenyl ester.

The amino group may be activated by known methods to those in the art, including converting the amino group into a phosphite amide, or by using the "phosphor-azo" method. See for both methods of activating: Houben-Weyl, Methoden der Organischen Chemie, 4th ed., Volume XV/2 (Georg Thieme Verlag).

The most usual methods for the above-noted condensation reactions are: the carbodi-imide method, the azide method, the mixed anhydride method, and the activated ester method, as described in E. Schröder and K. Lubke, "The Peptides", Volume I, 1965 (Academic Press). The so-called "solid phase" method of Merrifield, described in 85 J. Amer. Chem. Soc. 2149 (1963), may furthermore also be used for the preparation of the peptides and peptide derivatives herein described.

The reactive groups which are not to participate in the condensation reaction are effectively protected by suitable so-called "protecting" or "protective" groups which in turn are later readily removed by hydrolysis or reduction. Thus a carboxyl group may be effectively protected by known methods, for example, esterification with at least a stochiometrically effective amount of methanol, ethanol, tertiary butanol, benzyl alcohol or p-nitrobenzyl alcohol, or in the alternative, by conversion by known means into an amide, as for example, described in Houben-Weyl, Methoden der Organischen Chemie, 4td ed., Volume XV/1, page 315 seq. This last protecting group is however very difficult to remove, so that it is recommendable that this group only be used to protect the carboxyl group of the C-terminal amino-acid in the final peptide or the γ-carboxyl group of the glutamic acid. In this case, the peptides synthesis leads directly to the amide of the peptide according to the general formula (I).

Groups which may effectively protect an amino group are generally suitable acid groups, for example, an acid group derived from suitable aliphatic, aromatic, araliphatic or heterocyclic carboxylic acids (such as acetic acid, benzoic acid, pyridine-carboxylic acid), or an acid group derived from carbonic acid (such as ethoxycarbonyl, benzyloxy-carbonyl, t-butyloxycarbonyl or p-methoxybenzyloxy-carbonyl), or an acid group derived from a sulphonic acid (such as benzenesulphonyl or p-toluene-sulphonyl). Other groups may also be used, such as substituted or unsubstituted aryl- or aralkyl-groups, for example benzyl and triphenyl-methyl, or groups such as o-nitrophenylsulphenyl or 2-benzoyl-1-methylvinyl. (See Houben-Weyl, Vol. XV/1, page 46 seq.).

It is preferably to protect also the ε-amino group of lysine, and optionally the hydroxyl groups of serine and threonine. This latter protection is however not invariably necessary. The usual protective groups in this connection are a tertiary-butyloxy-carbonyl or a tosyl moiety for the ε-amino group of lysine, and a t-butyl or benzyl moiety for the hydroxyl group of serine and threonine.

The protecting groups may be cleaved by various conventional methods, depending on the nature of the group concerned, for example with the aid of trifluoroacetic acid, or by mild reduction, for example with hydrogen and a catalyst, such as palladium, or with HBr in glacial acetic acid.

Peptides according to the present invention with the amino-acid residue L-Met(O) may be prepared from the corresponding Met-containing peptide by mild oxidation using methods known in the art, for example with dilute hydrogen peroxide or a peracid. Such an oxidation results in a mixture of the S- and R-sulphoxide, which can be resolved into the separate diastereo-isomers by known methods, for example by selective crystallization. The separate diastereo-isomers may also be obtained directly by use of L-methionine-S (or R)-sulphoxide in the peptide synthesis.

The sulphone-peptides according to the present invention with the amino-acid residue $Met(O_2)$ may be obtained by oxidation of the corresponding Met-peptide I or by use of methionine-sulphone in the peptide synthesis.

Under the term suitable functional derivatives of the peptides according to the general formula (I) are understood:

(a) salts of the peptides according to the invention, in particular the acid addition salts and metal salts;

(b) esters preferably derived from aliphatic alcohols with one to about eighteen carbon atoms, in particular from alkanols with one to about six atoms, such as methanol, ethanol, propanol, isopropanol, butanol, sec. butyl alcohol, amyl alcohol, iso-amyl alcohol and hexyl alcohol;

(c) amides or mono or di-alkyl-substituted amides, where the alkyl group(s) posses(es) 1 to about 6 carbon atoms; preferably methyl or ethyl;

(d) N-acyl derivatives, derived from an aliphatic carboxylic acid with one to about six carbons;

(e) N-alkyl or N,N-dialkyl derivatives, in which the alkyl group has 1–6 and preferably 1–4 carbon atoms; and (f) metal complexes, formed by bringing the peptides herein referred to into contact with a sparingly soluble salt, hydroxide or oxide of a metal, preferably zinc.

Salts may be obtained directly from the reaction milieu in which the peptides are prepared or they may be prepared later by the reaction of the peptide with a base.

The acid addition salts may be obtained directly by isolating the peptide from the desired acid milieu, or the peptide obtained may be converted later into an acid addition salt by reaction of the peptide with an acid such as HCl, HBr, phosphoric acid, sulphuric acid, acetic acid, maleic acid, tartaric acid, citric acid, polyglutamic acid, or carboxymethylcellulose etc.

The metal salts, in particular the alkali metal salts, are obtained by reaction of the peptide with the desired metal base, such as NaOH, $Na_2CO_3$, $NaHCO_3$, etc.

N-acyl derivatives and preferably the N-terminal acyl derivatives, can be prepared by the use in the peptide synthesis of an amino-acid which already bears the acyl group concerned. This acyl group then also functions as a protective group in the peptide synthesis. In this way, the desired acyl derivatives is prepared directly. It is however also possible to introduce the desired acyl group later, by acylating the peptide in the usual way known to those in the art.

The N-acyl group which is most preferred is the acetyl group.

Esters and amides are also preferably prepared by using in the peptide synthesis an amino-acid which already bears the desired ester or amide group; they may however also be prepared later by esterifying the peptide obtained in the usual way known to those in the art, or by converting the same into an amide.

Amides which are most preferred are the unsubstituted amides and the mono-methyl- or dimethyl-amides, and the mono-ethyl- or diethyl-amides.

The N-alkyl and N,N-dialkyl derivatives, such as the N-monomethyl or N,N-dimethyl derivatives are prepared by using in the peptide synthesis the relevant, already N-mono or, as the case may be, N,N-dialkylated amino acid.

The metal complexes may be obtained by bringing the peptide into contact with sparingly soluble metal salts, metal hydroxides or metal oxides. The metal phosphates, metal pyrophosphates and metal polyphosphates are generally used as sparingly soluble metal salts. The metals which may be used in this process are the metals which belong to the "b" subgroups of the Periodic Table, for example cobalt, nickel, copper, iron and preferably zinc, as well as metals from the main groups of the Periodic Table which are capable of forming complexes, such as magnesium and aluminium. The preparation of these metal complexes takes place in the usual way. A metal complex may for example be obtained by addition of the peptide and a sparingly soluble metal salt, metal hydroxide, or metal oxide to an aqueous medium. The metal complex may also be obtained by addition of an alkaline medium to an aqueous solution of the peptide and a soluble metal salt, such that the insoluble peptide metal hydroxide complex is formed. The metal complex may furthermore be obtained by addition of the peptide, a soluble metal salt and a further soluble salt to an aqueous, preferably alkaline, medium, such that an insoluble peptide-metal salt complex is formed "in situ".

The metal complexes may be used directly without further processing as suspensions, or they may for example be freeze-dried and later resuspended.

The peptides according to general formula I, and the functional derivatives as defined above, accelerate the extinction of the avoidance response in rats in the so-called "pole-jumping" test in the same manner and on about the same level as the peptides described in Dutch application No. 78.02289. The present peptides are, however, not only shorter and can thus be prepared more economically, but the risk of side-effects due to peptide-fragments formed by metabolic degradation is appreciably reduced.

The present peptides are furthermore active in the so-called "grip-test". The rats treated with the peptides according to the invention hang suspended above the floor of the cage with their front paws grasping a pencil for a significantly longer time than rats treated with saline (placebo) or α-endorphin.

This pharmacological profile renders the peptides and peptide derivatives, herein referred to, particularly suitable for use in the treatment of certain mental disorders in which a reduction of the cerebal functions is desired. In particular the present peptides have neuroleptic activity and may thus be suitable in the treatment of for example certain schizophrenic syndromes.

The peptides are used in effective amounts with known carriers, and preferably used in a dosage of 1 μg to 1 mg per kg body weight per day, depending on the form in which they are administered. Humans are preferably treated with a daily dosage of 0.1 mg to about 10 mg, more particularly between 0.5 and 2 mg.

The peptides according to the invention may be administered by either the oral, rectal or the parenteral routes, by means of a pharmaceutically effective carrier known to those in the art. The peptides are preferably used as injectable preparations. For the purposes of injection they are dissolved, suspended or emulsified in a suitable fluid. Mixed with suitable excipients and fillers, the peptides herein referred to may further be provided in a form suitable for oral administration, such as pills, tablets, dragees or capsules. The peptides herein described may furthermore be administered in the form of a suppository or spray.

Particularly valuable preparations are obtained when the peptides herein referred to are provided in a form conferring prolongation of activity. Preferably, the metal complexes are used. These metal complexes may be obtained by bringing the peptides into contact with sparingly soluble metal salts, metal hydroxides or oxides known to those in the art. The metal phosphates, metal pyrophosphates and metal polyphosphates are generally used as sparingly soluble metal salts.

Peptides of the general formula I, which are preferred, are those peptides in which $R_1$ represents the amino-acid radical L-Gln, R is the amino-acid radical L-Lys, and B is the group L-Leu-OH, or L-Leu-L-Phe-L-Lys-OH.

With respect to the group A in the peptides according to the invention, that peptide is particularly preferred in which A represents the peptide radical: $Z_2$-L-Ser-L-Glu- wherein $Z_2$ preferably represents the residue H-L-Thr or H-D-Thr, but also the slightly longer peptide radicals A merit special recommendation, especially those radicals wherein A represents:

H-$Q_1$-L-Thr-L-Ser-L-Glu- $Q_2$-L-Thr-L-Ser-L-Glu- and $Z_3$-$Q_1$-L-Thr-L-Ser-L-Glu-, in which preferably $Q_1$ is L-Met, L-Met(O) or L-Met($O_2$), $Q_2$ is desamino Met, desamino Met($O_2$) or ε-aminocaproyl, $Z_3$ is H-L-Phe, desamino Phe or β-Ala.

The radical $H_2N$-ALK-CO, in which ALK is an (1–6 C) alkylene or alkylidene group, includes inter alia the amino acid residues glycyl, alanyl, β-alanyl, valyl, leucyl, isoleucyl, ε-amino caproyl and α-methylleucyl.

The respect to the examples below, the following observations and rules are made:

I. If no optical configuration is given, the L-form is exemplified.

II. The following abbreviations have been used for the protecting or activating groups employed:
Boc = tertiary butyloxycarbonyl
tBu = tertiary butyl
Me = methyl
ONp = p-nitrophenyloxy
Z = benzyloxycarbonyl III. The following abbreviations have been assigned to the solvents or reagents used:
To = toluene
EtOH = ethanol
Bu = butanol
Py = pyridine
Ac = acetic acid or acetyl
EtOAc = ethyl acetate
Am = amyl alcohol
I.A.N. or IAN = iso-amyl nitrite
DMF = dimethylformamide
THF = tetrahydrofuran
DCCI = dicyclohexylcarbodi-imide
DCHU = dicyclohexylurea
TEA = triethylamine
TFA = trifluoro-acetic acid
Wa = water
N.E.M. = N-ethylmorpholine
HOBt = N-hydroxybenztriazole IV. The following abbreviations have been used for the amino-acid groups:
Met = methionyl
Met(O) = sulphoxide of methionyl
Met(O₂) = sulphone of methionyl
Phe = phenylalanyl
Pro = prolyl
Ser = seryl
Lys = lysyl
Arg = arginyl
Thr = threonyl
Glu = glutamyl
Gln = glutaminyl
Gly = glycyl
Val = valyl
Leu = leucyl
Ala = alanyl
MeLeu = α-methylleucyl.

EXAMPLES

Starting substances

A. Synthesis Boc-Gly-Phe-Met-OH and Boc-Phe-Met-analogues (1) H-Phe-Met-OMe.HCl 11.83 g Boc-Phe-Met-OMe (Biochemistry 8, 4183 (1969) is dissolved in 100 ml methylenechloride, after which HCl is passed into the solution for about 40 minutes. After evaporation of the solution to dryness 75 ml ethylacetate is added, resulting in a precipitate. The solid substance is filtered, washed with petroleum-ether and dried.

$R_f$ in To:EtOH (8:2)=0.43 on $SiO_2$.
Melting point 123°-124° C.

(2) Boc-Gly-Phe-Met-OMe 3.5 g Boc-Gly-OH is dissolved in 30 ml DMF and cooled to 0° C., after which 1 eq. TEA is added. The mixture is further cooled to −10° C., after which 1 eq. ethylchloroformate is added. The mixture is stirred for 10 minutes. Then 6.6 g H-Phe-Met-OMe.HCl (A. 1) in 30 ml DMF and 1.1 eq. TEA are added to the mixture, which is stirred at −10° C. for half an hour and then at room temperature for 20 hours. After cooling to −10° C. TEA.HCl is filtered off and the filtrate is evaporated to dryness. The residue is dissolved in 225 ml ethylacetate and 55 ml water and washed successively with 30% Na-Cl-solution, 0.1 N HCl, 30% NaCl-solution, 5% $NaHCO_3$-solution and 30% NaCl-solution. The solution is subsequently dried over $Na_2SO_4$, filtered and evaporated to dryness.

$R_f$ in To:EtOH (8:2)=0.49 on $SiO_2$.

(3) Boc-Gly-Phe-Met-OH

The peptide obtained sub A. 2 is dissolved in 30 ml dioxane/$H_2O$ (9:1). After the addition of 1.2 eq. 2.17 N NaOH the mixture is stirred at room temperature for one hour, brought to pH=6 and evaporated to dryness. The residue is then dissolved in 50 ml EtOAc, after which the pH is set to 2 by 1 N HCl. After washing with 30% NaCl (three times), drying on $Na_2SO_4$ and filtering off, the solution is evaporated to dryness.

$R_f$=0.62. Yield 95%.

(4) Hydrolysis (in the manner described in A. 3) of the corresponding methylesters yields the following protected peptides:

| | |
|---|---|
| Boc—Leu—Phe—Met—OH; | $R_f$ = 0.48 |
| Boc—Ala—Phe—Met—OH; | $R_f$ = 0.45 |
| Desamino—Phe—Met—OH; | $R_f$ = 0.78 |
| Boc—Phe—Met—OH; | $R_f$ = 0.76 |
| Boc—D-Phe—Met—OH; | $R_f$ = 0.80 |

In A. 3 and A. 4 the system is: $CHCl_3$/MeOH/Wa (70:30:5) on $SiO_2$.

B. Synthesis H-Thr-Ser-Glu(OtBu)-Lys(Boc)-OMe and analogues (1) H-Glu(OtBu)-Lys(Boc)-OMe (a) 35.3 g Z-Glu(OtBu)-OH and 27.0 g HOBt are dissolved in 150 ml DMF, after which the mixture is cooled to about −22° C. 29.7 g H-Lys(Boc)-OMe.HCl in 100 ml DMF and 1 eq. NEM is then added to the cooled mixture. The pH of the mixture is adjusted to 6.4 with NEM and 23 g DCCI is then added. After stirring for about 15 minutes at about −22° C. and about 12 hours at room temperature, DCHU is separated by filtration and the filtrate is evaporated to dryness.

The residue is dissolved in 400 ml EtOAc and washed subsequently with 15% NaCl solution, 5% $KHSO_4$ solution, 5% $NaHCO_3$ solution and 15% NaCl solution. After drying and filtering, the filtrate is evaporated to dryness. The residue is crystallized from ether/petroleum ether (1:2). Yield 86.6%; melting point 54°–56° C.

(b) The peptide obtained in B(1) is dissolved in DMF, after which Pd/C (10%) is added and $H_2$ is passed through until the evolution of $CO_2$ ceases. After filtering, the filtrate is evaporated to dryness.

$R_f$ in To:EtOH (8:2)=0.24 on $SiO_2$.

(2) Z-Thr-Ser-$N_2H_3$ 38.05 g Z-Thr-Ser-OMe (See Recueil 83, 255, (1964), incorporated herein) is dissolved in 12 ml ethanol, after which 43 ml hydrazine hydrate is added. After stirring for about 2 hours, the solid substance is separated by filtration, washed with ethanol/ether (1:1) and dried.

$R_f$ in $CHCl_3:CH_3OH:Wa$ (70:30:5)=0.58 on $SiO_2$; decomposition 215°-216° C.

(3a) Z-Thr-Ser-Glu(OtBu)-Lys(Boc)-OMe (a) 1.22 g of the hydrazide obtained in B(2) is suspended in 15 ml DMF after which 4.28 ml 2.42 N HCl/DMF is added. The clear solution is cooled to about −20° C. 0.7 ml IAN is then added and the mixture is stirred for about 30 minutes at about −20° C.

1.5 g of the peptide obtained in B(1) in 10 ml DMF is then added. The pH of the reaction mixture is then adjusted to 7.2, and the whole is placed in a refrigerator for about 6 days. The solvent is then removed by evaporation, the residue is dissolved in EtOAc and the resultant solution is washed. Evaporation to dryness gives a solid substance. Yield 61.9%; melting point 130°-132° C.

(3b) H-Thr-Ser-Glu(OtBu)-Lys(Boc)-OMe

In a way similar to that described in B(1)(b) the Z-protected peptide is hydrogenated in methanol with palladium on charcoal as catalyst. Yield 99%; $R_f$ in Bu:Py:Ac:Wa (38:24:8:30)=0.73 on $SiO_2$.

(4) The following protected peptides are obtained in analogous ways:
desamino-Thr-Ser-Glu(OtBu)-Lys(Boc)-OMe
$R_f$ in Bu:Py:Ac:Wa (38:24:8:30)=0.80 on $SiO_2$;
H-β-Ala-Ser-Glu(OtBu)-Lys(Boc)-OMe
$R_f$ in Bu-py-Ac-Wa(38:24:8;30)=0.66
H-Ala-Ser-Glu(OtBu)-Lys(Boc)-OMe
$R_f$ in Bu:Py:Ac:Wa (38:24:8:30)=0.65 on $SiO_2$.

C. Synthesis Z-Ser-$R_1$-Thr-Pro-OH ($R_2$=Glu or Gln)

(1) H-Thr-Pro-OtBu

In the way described in B(1), 0.33 mol Z-Thr-OH and 0.35 mol H-Pro-OtBu are coupled with the aid of HOBt and DCCI in DMF. Yield 64%; melting point 65°-67° C. The Z-Thr-Pro-OtBu obtained in this way is hydrogenated in the way described above (see B.3.b.).

$R_f$ in To:EtOH (8:2)=0.10 on $SiO_2$.

(2) H-Gln-Thr-Pro-OtBu 1.36 g H-Thr-Pro-OtBu is dissolved in 10 ml DMF, after which 1.93 g Z-Gln-ONp is added and the reaction mixture is stirred for about 20 hours at room temperature. After evaporation of the mixture to dryness, the residue is dissolved in EtOAc and washed consecutively with 5% $KHSO_4$ solution, 5% $NaHCO_3$ solution and a saturated NaCl solution. The solution is then dried over $Na_2SO_4$ and filtered, and the filtrate is evaporated to dryness.

Melting point 89°-90° C.; yield 59%. The Z-protected peptide obtained is hydrogenated in DMF in the way described above.

$R_f$ in $CHCl_3:CH_3OH$ (8:2)=0.08 on $SiO_2$.

(3) Z-Ser-Gln-Thr-Pro-OtBu

In a way analogous to that described in C (1), 20.5 g Z-Ser-OH is coupled with the peptide obtained in C (2) with the aid of DCCI and HOBt.

Yield 70%. Melting point 104°-106° C.

(4) Z-Ser-Gln-Thr-Pro-OH 1.43 g of the peptide obtained in C (3) is stirred in 15 ml 90% TFA at room temperature for about 30 minutes. The mixture is then poured into ether. The solid material is separated by filtration, washed with ether and dried. Yield 90%; melting point 111°-113° C.

$R_f$ in $CHCl_3:CH_3OH:Wa$ (70:30:5)=0.23 on $SiO_2$.

(5) Z-Ser-Glu(OtBu)-Thr-Pro-OH

H-Thr-Pro-OMe, obtained by coupling Z-Thr-OH and H-Pro-OMe with the aid of the HOBt/DCCI method followed by hydrogenation, is consecutively coupled with Z-Glu(OtBu)-OH and Z-Ser-OH. Both coupling reactions are performed by the HOBt/DCCI method, and after the first coupling of Z-protected peptide obtained is hydrogenated. The resultant peptide, Z-Ser-Glu(OtBu)-Thr-Pro-OMe, is subsequently saponified by dissolving in dioxan/water (9:1) and addition of 0.2 N NaOH according to the method described in A (3).

$R_f$ in $CHCl_3:CH_3OH:Wa$ (70:30:5)=0.29 on $SiO_2$.

D. Synthesis of H-Leu-Val-Thr-(L or D)-Leu-OtBu (1) H-Thr-Leu-OtBu

In a way corresponding to that described in J.A.C.S. 95, 877 (1973), incorporated herein, Z-Thr-Leu-OtBu is prepared via the HOBt/DCCI coupling method.

Melting point 81.5°-83° C.

The Z-protected dipeptide is then hydrogenated in the way described above. Yield 100%; $R_f$ in To:EtOH (8:2)=0.20 on $SiO_2$.

(2) H-Thr-D-Leu-OtBu

Obtained by hydrogenation of Z-Thr-D-Leu-OtBu with melting point 89°-92° C.

$R_f$ in To:EtOH (8:2)=0.18 on $SiO_2$.

(3) H-Val-Thr-Leu-OtBu

Coupling of 7.85 g Z-Val-ONp with 5.53 g H-Thr-Leu-OtBu in 160 ml DMF in the way described in C (2) provides Z-Val-Thr-Leu-OtBu in 72% yield.

Melting point 127°-129° C.

Hydrogenation of this Z-protected peptide in methanol gives 9.1 g of an oily product.

$R_f$ in $CHCl_3:CH_3OH$ (8:2)=0.60 on $SiO_2$.

(4) H-Val-Thr-D-Leu-OtBu

Obtained in a way analogous to that described in D (3).

$R_f$ in $CHCl_3:CH_3OH$ (8:2)=0.55 on $SiO_2$.

(5) H-Leu-Val-Thr-Leu-OtBu

Coupling of 6.7 g Z-Leu-ONp and 6.1 g of the peptide obtained in D (3), in 160 ml DMF, in the way described in C (2), gives the Z-protected peptide in a yield of 7.7 g (77%).

Melting point 153°-155° C.

This Z-protected peptide is hydrogenated in methanol. $R_f$=0.75 on $SiO_2$. In an analogous manner the following peptides are prepared:

(6) H-Leu-Val-Thr-D-Leu-OtBu
$R_f$=0.80.

(7) H-Leu-Val-Thr-MeLeu-OtBu
$R_f$=0.68.

$R_f$ in $CHCl_3:CH_3OH:Wa$ (70:30:5) on $SiO_2$.

E. Synthesis of Boc-Gly-Phe-Met-Thr-Ser-Glu(OtBu)-Lys(Boc)-OMe and analogues (1) Boc-Gly-Phe-Met-Thr-Ser-Glu(OtBu)-Lys(Boc)-OMe 2.1 g Boc-Gly-Phe-Met-OH, A (3), and 3.15 g H-Thr-Ser-Glu(OtBu)-Lys(Boc)-OMe, B (3), are coupled with the aid of 2 eq. HOBt and 1 eq. DCCI in the way described in B (1). After removal of the DCHU by filtration, the filtrate is evaporated to dryness and the residue is crystallized from methanol.

Melting point 191°-193° C. (decomposition); yield 61%.

(2) Boc-Gly-Phe-Met-Thr-Ser-Glu(OtBu)-Lys(Boc)-OH 2.67 g of the peptide obtained in E (1) is dissolved in 30 ml dioxan/water (9:1) after which 13.8 ml 0.217 g NaOH is added to the solution. The reaction mixture is stirred for 18 minutes at room temperature. The pH of the mixture is then adjusted to 2 with 1 N HCl. After the addition of about 10 ml water, a solid crystallizes and this is filtered off and dried. Yield 80%.

$R_f$ in $CHCl_3:CH_3OH:Wa$ (70:30:5)=0.58 on $SiO_2$.

The following peptides are prepared in a corresponding way:

(3) Boc-Ala-Phe-Met-Thr-Ser-Glu(OtBu)-Lys(Boc)-OH $R_f$ in $CHCl_3:CH_3OH:Wa$ (70:30:5)=0.64 on $SiO_2$.

(4) Boc-Leu-Phe-Met-Thr-Ser-Glu(OtBu)-Lys(Boc)-OH $R_f$ in $CHCl_3:CH_3OH:Wa$ (70:30:5)=0.67 on $SiO_2$.

F. Synthesis of
H-Ser-$R_1$-Thr-Pro-Leu-Val-Thr-Leu-OtBu
($R_1$=Glu(OtBu) or Gln) and analogues (1) H-Ser-Gln-Thr-Pro-Leu-Val-Thr-Leu-OtBu 1.17 g Z-Ser-Gln-Thr-Pro-OH of C (4) is coupled to 930 mg H-Leu-Val-Thr-Leu-OtBu D (5) with the aid of 2 eq. HOBt and 1 eq. DCCI, according to the method described in B (1). After removal by filtration of the DCHU formed, the filtrate is evaporated to dryness and dissolved in a mixture of sec. butanol and $CHCl_3$ (2:3), after which the solution is washed and evaporated to dryness. The residue is crystallized from DMF/EtOAc (1:20); melting point 210°–212° C. Yield 72%.

The Z-protected peptide obtained is hydrogenated in methanol in the way described above. Yield 86%.

$R_f$ in $CHCl_3:CH_3OH:Wa$ (70:30:5)=0.25 on $SiO_2$.

The following peptides are prepared in a corresponding way:

(2) H-Ser-Glu(OtBu)-Thr-Pro-Leu-Val-Thr-Leu-OtBu $R_f$ in $CHCl_3:CH_3OH:Wa$ (70:30:5)=0.35 on $SiO_2$.

(3) H-Ser-Gln-Thr-Pro-Leu-Val-Thr-D-Leu-OtBu $R_f$ in $CHCl_3:CH_3OH:Wa$ (70:30:5)=0.30 on $SiO_2$.

(4) H-Ser-Gln-Thr-Pro-Leu-Val-Thr-Leu-NHCH$_3$ 100 mg of the peptide Z-Ser-Gln-Thr-Pro-Leu-Val-Thr-Leu-OH (see F. 5) is dissolved in 2 ml DMF, after which the solution is cooled to about −10° C. 1 eq. TEA and 1 eq. ethylchloroformate are then added, after which the mixture is stirred for 10 minutes. After addition of an excess of monomethylamine, the mixture is stirred for about 30 minutes at about −10° C. and 2 hours at 0° C., after which the whole is evaporated to dryness. The residue is dissolved in a mixture of sec. butanol and chloroform (2:3), after which the solution is washed, dried, and evaporated to dryness. Yield 65 mg, melting point 223°–225° C.

The Z-protected peptide-monomethylamide obtained is hydrogenated in DMF in the usual way.

$R_f$ in $CHCl_3:CH_3OH:Wa$ (70:30:5)=0.26 on $SiO_2$.

(5) H-Ser-Gln-Thr-Pro-Leu-Val-Thr-Leu-OMe 100 mg of the peptide Z-Ser-Gln-Thr-Pro-Leu-Val-Thr-Leu-OtBu (see F (1)) in 2 ml 90% TFA is stirred for 20 minutes at room temperature. The mixture is then evaporated to dryness and the solid material is filtered off and dried. The solid (80 mg) is dissolved in DMF and esterified with caesium carbonate and methyl iodide by the method described in J.O.C. 42, 1286 (1977). The Z-protected peptide methyl-ester is then hydrogenated in DMF in the usual way; yield 45 mg.

$R_f$ in $CHCl_3:CH_3OH:Wa$ (70:30:5)=0.34 on $SiO_2$.

(6) H-Ser-Gln-Thr-Pro-Leu-Val-Thr-Leu-Phe-Lys(Boc)-OtBu 0.992 g Z-Ser-Gln-Thr-Pro-Leu-Val-Thr-Leu-OH of F (5) is coupled to 540 mg H-Phe-Lys(Boc)-OtBu in DMF with the aid of DCCI (1 eq.) and HOBt (2 eq.). After removal of the DCHU by filtration, the filtrate is evaporated to dryness. The residue is subsequently dissolved in 75 ml sec. butanol/chloroform (2:3) and the solution washed with water, 0.1 N HCl, 5% NaCl solution and water, after which it is dried over $Na_2SO_4$, filtered and the filtrate evaporated to dryness. Yield of Z-Ser-Gln-Thr-Pro-Leu-Val-Thr-Leu-Phe-Lys(Boc)-OtBu: 1 g; melting point 221°–222° C. (decomposition). This peptide is hydrogenated in DMF with Pd/C as catalyst in the way described above.

$R_f$ in $CHCl_3:CH_3OH:Wa$ (70:30:5)=0.27 on $SiO_2$. In an analogous manner are prepared:

(7) H-Ser-Gln-Thr-Pro-Leu-Val-Thr-Leu-Phe-OtBu $R_f$=0.34 on $SiO_2$ (system $CHCl_3:CH_3OH:Wa$ 70:30:5).

(8) H-Ser-Gln-Thr-Pro-Leu-Val-Thr-MeLeu-OtBu $R_f$=0.30 on $SiO_2$ (system $CHCl_3:CH_3OH:Wa$ 70:30:5).

EXAMPLE I

Synthesis
H-Gly-Phe-Met-Thr-Ser-Glu-Lys-Ser-Gln-Thr-Pro-Leu-Val-Thr-Leu-OH 1.22 g Boc-Gly-Phe-Met-Thr-Ser-Glu(OtBu)-Lys(Boc)OH (E. 2) and 308 mg HOBt are dissolved in 10 ml DMF and the mixture is then cooled to −22° C. Then 1.05 g H-Ser-Gln-Thr-Pro-Leu-Val-Thr-Leu-OtBu (F. 1) in 5 ml DMF and 1 eq. NEM are added to the cooled mixture. The pH of the mixture is set to 6.5 with NEM, after which 271 mg DCCI is added. After stirring at −22° C. for 15 minutes and subsequently at room temperature for 8 hours and at 35° C. for 12 hours, under $N_2$, the DCHU formed is filtered out and the filtrate is poured out in water.

The resultant precipitate is washed and dried. Yield 78%. Decomposition at 205° C. to 208° C.

$R_f$ in $CHCl_3:CH_3OH:Wa$ (70:30:5)=0.77 on $SiO_2$.

1.6 g Of the resultant, protected peptide are introduced into 30 ml 90% TFA, after which a few drops of tertiary butylsulphide are added. The mixture is stirred at room temperature for 1 hour and then poured out in ether. The resultant solid substance is filtered out and dried. The substance is then dissolved in 30 ml of tertiary butanol/water (1:1), after which an ion exchange in the form of an acetate (Lewatit$^{(R)}$) is added and the mixture is stirred for half an hour. The ion exchanger is then filtered off and the filtrate is evaporated to dryness. Yield 1.34 g.

$R_f$ in Bu:Py:Ac:Wa (2:3/4:1/4:1)=0.25 on $SiO_2$.

The substance is purified through countercurrent distribution in the solvent system Bu:Ac:Wa (4:1:5). Yield 600 mg.

EXAMPLE II

In a manner corresponding to Example I are produced:

1. H-Gly-Phe-Met-Thr-Ser-Glu-Lys-Ser-Gln-Thr-Pro-Leu-Val-Thr-Leu-OMe
(E. 2+F. 5) $R_f$=0.46
2. H-Ala-Phe-Met-Thr-Ser-Glu-Lys-Ser-Gln-Thr-Pro-Leu-Val-Thr-Leu-NHCH$_3$
(E. 3+F. 4) $R_f$=0.31
3. H-Leu-Phe-Met-Thr-Ser-Glu-Lys-Ser-Gln-Thr-Pro-Leu-Val-Thr-Leu-OH
(E. 4+F. 1) $R_f$=0.33

4. H-Gly-Phe-Met-Thr-Ser-Glu-Lys-Ser-Gln-Thr-Pro-Leu-Val-Thr-MeLeu-OH
(E. 2+F. 8) $R_f=0,26$
5. H-Gly-Phe-Met-Thr-Ser-Glu-Lys-Ser-Gln-Thr-Pro-Leu-Val-Thr-Leu-OH
(E. 2+F. 2) $R_f=0,22$
6. H-Ala-Phe-Met-Thr-Ser-Glu-Lys-Ser-Gln-Thr-Pro-Leu-Val-Thr-D-Leu-OH
(E. 3+F. 3) $R_f=0.34$.
$R_f$ in Bu:Py:Ac:Wa (2:3/4:1/4:1).

EXAMPLE III

H-Phe-Met-Thr-Ser-Glu-Lys-Ser-Gln-Thr-Pro-Leu-Val-Thr-Lue-OH

1. Boc-Phe-Met-Thr-Ser-Glu(OtBu)-Lys(Boc)-OH

In the manner described in E. 1 and E. 2, Boc-Phe-Met-OH (A. 4) is condensed with H-Thr-Ser-Glu (Otbu)-Lys(Boc)-OMe and the resultant peptide is saponified.

$R_f$ in $CHCL_3$:MeOH:Wa (70:30:5) = 0.68 on $SiO_2$.

2. Coupling of the peptide obtained sub 1 with H-Ser-Gln-Thr-Pro-Leu-Val-Thr-Leu-OtBu (F. 1) and removal of the protection of the peptide thus obtained in the manner described in Example I provides the peptide of the heading.

$R_f$ in Bu:Py:Ac:Wa (2:3/4:1/4:1) = 0.34 on $SiO_2$.

EXAMPLE IV

In the same manner as described in Example III are produced:
Desamino-Phe-Met-Thr-Ser-Glu-Lys-Ser-Gln-Thr-Pro-Leu-Val-Thr-Leu-OH.
H-D-Phe-Met-Thr-Ser-Glu-Lys-Ser-Gln-Thr-Pro-Leu-Val-Thr-Leu-OH.

EXAMPLE V

H-Thr-Ser-Glu-Lys-Ser-Gln-Thr-Pro-Leu-Val-Thr-Leu-OH

1. Z-Thr-Ser-Glu(OtBu)-Lys(Boc)-$N_2H_3$ 4.0 g Z-Thr-Ser-Glu(OtBu)-Lys(Boc)-OMe (B. 3.a) is dissolved in 40 ml of methanol. Thereto is added 2.0 ml $N_2H_4.H_2O$, after which the mixture is stirred at room temperature for 18 hours. The resultant solid substance is filtered out and then stirred with 100 ml $H_2O$. The solid substance is again filtered out, washed with water and dried.

Yield 3.5 g. Melting point 158° C. to 159° C.

$R_f$ in $CHCl_3$/MeOH (8:2) = 0.55 on $SiO_2$.

2. Z-Thr-Ser-Glu(OtBu)-Lys(Boc)-Ser-Gln-Thr-Pro-Leu-Val-Thr-Leu-OtBu.

1.42 g Z-Thr-Ser-Glu(OtBu)-Lys(Boc)-$N_2H_3$ is dissolved in 10 ml DMF. Subsequently the solution is cooled to 0° C. and then 1.62 ml 2,3 N HCl/DMF is added and after cooling to −20° C. 0.27 ml I.A.N. is added. The mixture is stirred at −15° C. to −20° C. for 5 minutes.

To this mixture are subsequently added 0.45 ml N.E.M. and a solution of 1.57 g H-Ser-Gln-Thr-Pro-Leu-Val-Thr-Leu-OtBu (F. 1) in 10 ml DMF. The reaction mixture is set to pH 7.0 to 7.2 and left standing at about 0° C. for three days. The mixture is then dropped into 310 ml $H_2O$. The resultant solid substance is isolated, washed with water and dried.

Yield 2.29 g. Melting point 185° C. to 187° C. (Decomposition).

$R_f$ in $CHCl_3$/MeOH (8:2) = 0.35 on $SiO_2$.

3. H-Thr-Ser-Glu-Lys-Ser-Gln-Thr-Pro-Leu-Val-Thr-Leu-OH 2.26 g (1.37 mmol) Z-Thr-Ser-Glu(OtBu)-Lys(Boc)-Ser-Gln-Thr-Pro-Leu-Val-Thr-Leu-OtBu is dissolved in 30 ml DMF, after which Pd/C (10%) is added and $H_2$ is led in until $CO_2$-development is no longer observed. After filtering out Pd/C the filtrate is reduced by evaporation.

The hydrogenated peptide is introduced into 30 ml 90% TFA and a few drops of anisol are added. The mixture is stirred at room temperature for 1 hour and then poured in ether. The substance is purified through counter-current distribution in the solvent system Bu:Ac:Wa (4:1:5).

The collected fractions are reduced by evaporation, dissolved in 50 ml of tertiary butanol/$H_2O$ (1:1), after which an ion exchanger in the form of acetate is added and the mixture is stirred for half an hour. The ion exchanger is then filtered out and the filtrate is frozen and freeze-dried. Yield 1.02 g.

$R_f$ in Bu:Py:Ac:Wa (2:3/4:1/4:1) = 0.17 on $SiO_2$.

EXAMPLE VI

In the same manner as described in Example V the following peptides are prepared:
H-D-Thr-Ser-Glu-Lys-Ser-Gln-Thr-Pro-Leu-Val-Thr-Leu-OH
$R_f=0.19$.
H-Thr-Ser-Glu-Lys-Ser-Gln-Thr-Pro-Leu-Val-D-Leu-OH
$R_f=0.18$.
H-Thr-Ser-Glu-Lys-Ser-Gln-Thr-Pro-Leu-Val-Thr-Leu-$NHCH_3$
$R_f=0.26$.
H-Thr-Ser-Glu-Lys-Ser-Gln-Thr-Pro-Leu-Val-Thr-Leu-OMe
$R_f=0.34$.
H-Thr-Ser-Glu-Lys-Ser-Gln-Thr-Pro-Leu-Val-Thr-Leu-Phe-Lys-OH
$R_f=0.15$.
H-Thr-Ser-Glu-Lys-Ser-Glu-Thr-Pro-Leu-Val-Thr-Leu-OH
$R_f=0.16$.
H-Thr-Ser-Glu-Lys-Ser-Gln-Thr-Pro-Leu-Val-Thr-MeLeu-OH
$R_f=0.23$.
H-Ala-Ser-Glu-Lys-Ser-Gln-Thr-Pro-Leu-Val-Thr-Leu-Phe-Lys-OH
$R_f=0.21$.
desamino Thr-Ser-Glu-Lys-Ser-Gln-Thr-Pro-Leu-Val-Thr-Leu-OH
$R_f=0.30$.
solvent system Bu:Py:Ac:Wa (2:3/4:1/4:1) in $SiO_2$

EXAMPLE VII

H-Lys-Ser-Gln-Thr-Pro-Leu-Val-Thr-Leu-OH

1. Z-Lys(Boc)-Ser-Gln-Thr-Pro-Leu-Val-Thr-Leu-OtBu 1.35 g Z-Lys(Boc)-ONp (2.7 mmol) and 2.42 g (2.64 mmol) H-Ser-Gln-Thr-Pro-Leu-Val-Thr-Leu-OtBu (F. 1) are dissolved in 35 ml DMF. After stirring at room temperature for 18 hours the reaction mixture is evaporated to dryness.

The residue is then dissolved in 25 ml MeOH, and the solution is poured out in ether (150 ml). The solid substance is isolated, washed with ether and dried, Yield 3.2 g. Melting point 197°–200° C. (Decomposition).

$R_f$ in CHCl$_3$/MeOH (8:2)=0.58 on SiO$_2$.

2. H-Lys(Boc)-Ser-Gln-Thr-Pro-Leu-Val-Thr-Leu-OtBu 1.0 g (0.78 mmol) of the protected peptide obtained sub 1 is dissolved in DMF and with the aid of Pd/C (10%) hydrogenated in the manner described in Example V. 3.

Yield 0.7 g. Melting point 197°–198° C. (Decomposition).

$R_f$ in CHCl$_3$/MeOH/Wa (70:30:5)=0.42 on SiO$_2$.

3. 0.65 g Of the peptide obtained sub 2 is introduced into 6.5 ml 90% TFA, after which a few drops of anisol are added. The mixture is stirred at room temperature for 45 minutes and dried. The solid substance is then dissolved in 15 ml of tertiary butanol/water (1:1) and subsequently an ion exchanger in acetate form is added and the mixture is stirred for half an hour. The ion exchanger is then filtered out and the filtrate is evaporated to dryness.

Yield 540 mg.

The substance is purified through counter-current distribution in the solvent Bu:Ac:Wa (4:1:5).

Yield 320 mg.

$R_f$ In Bu:Py:Ac:Wa (2:3/4:1/4:1)=0.19 on SiO$_2$.

EXAMPLE VIII

In the same manner as described in Example VII the following peptides are prepared:

H-Lys-Ser-Gin-Thr-Pro-Leu-Val-Thr-Leu-OMe
  (Lys+F. 5)
  $R_f$=0.26

H-Lys-Ser-Gln-Thr-Pro-Leu-Val-Thr-Leu-Phe-Lys-OH
  (Lys+F. 6)
  $R_f$=0.16

H-Lys-Ser-Gln-Thr-Pro-Leu-Val-Thr-D-Leu-OH
  (Lys+F. 3)
  $R_f$=0.21

R$_4$-values in Bu:Py:Ac:Wa (2:3/4:1/4:1) on SiO$_2$.

EXAMPLE IX

H-Glu-Lys-Ser-Gln-Thr-Pro-Leu-Val-Thr-Leu-OH

1. Z-Glu(OtBu)-Lys(Boc)-Ser-Gln-Thr-Pro-Leu-Val-Thr-Leu-OtBu 843 mg Z-Glu(OtBU)-OH and 676 mg HOBt are dissolved in 10 ml DMF. After cooling to −22° C., 2.82 g H-Lys(Boc)-Ser-Gln-Thr-Pro-Leu-Val-Thr-Leu-OtBu (Example VII.2) and 517 mg DCCI, dissolved in 2 ml DMF, are added to the solution. After stirring at −22° C. for some time, the DCHU is filtered out and the filtrate is evaporated to dryness.

$R_f$ in CHCl$_3$:MeOH (8:2)=0.52 on SiO$_2$.

Yield 2.7 g. Melting point 196° C. to 199° C.

2. In the manner described in Example V. 3 the protected peptide obtained sub 1 is deprived of the protecting groups and then purified.

Yield 80 mg. $R_f$ in Bu:Py:Ac:Wa (2:3/4:1/4:1)=0.14 on SiO$_2$.

EXAMPLE X

H-Ser-Glu-Lys-Ser-Gln-Thr-Pro-Leu-Val-Thr-Leu-OH

In the same manner as described in Example IX the protected product of the heading is obtained by coupling the Z-Ser-OH with H-Glu(OtBu)-Lys(Boc)-Ser-Gin-Thr-Pro-Leu-Val-Thr-Leu-OtBu (see Ex. IX)

The removal of the protected groups is carried out in the manner described in Example V. 3.

$R_f$ in Bu:Py:Ac:Wa (2:3/4:1/4:1)=0.19 on SiO$_2$.

EXAMPLE XI

H-Met-Thr-Ser-Glu-Lys-Ser-Gln-Thr-Pro-Leu-Val-Thr-Leu-OH

1. Boc-Met-Thr-Ser-Glu(OtBu)-Lys(Boc)-OH

Boc-Met-OH is coupled in the manner described in E. 1 with H-Thr-Ser-Glu(OtBu)-Lys(Boc)-OMe (B.3.b), after which the resultant peptide methylester is saponified in the manner described in E.2.

2. In full analogy with the synthesis described in Example I the peptide obtained sub 1 is coupled with H-Ser-Gln-Thr-Pro-Leu-Val-Thr-Leu-OtBu (F. 1), after which the resultant protected peptide is deprived of the protecting groups and purified.

$R_f$ in Bu:Py:Ac:Wa (2:3/4:1/4:1)=0.20 on SiO$_2$.

EXAMPLE XII

In a similar manner are produced:

H-Met-Thr-Ser-Glu-Lys-Ser-Gln-Thr-Pro-Leu-Val-Thr-Leu-Phe-OH
  $R_f$=0.26.

H-Met-Thr-Ser-Glu-Lys-Ser-Gln-Thr-Pro-Leu-Val-Thr-D-Leu-OH,
  $F_f$=0.22.

H-D-Met-Thr-Ser-Glu-Lys-Ser-Gln-Thr-Pro-Leu-Val-Thr-Leu-OH,
  $R_f$=0,21.

β-Ala-Thr-Ser-Glu-Lys-Ser-Gln-Tru-Pro-Leu-Val-Thr-Leu-OH,
  $R_f$=0,16.

desamino-Met-Thr-Ser-Glu-Lys-Ser-Gln-Thr-Pro-Leu-Val-Thr-Leu-OH
  $R_f$=0.31.

6-aminohexanoyl-Thr-Ser-Glu-Lys-Ser-Gln-Thr-Pro-Leu-Val-Thr-Leu-OH
  $R_f$=0.18.

H-Leu-Thr-Ser-Glu-Lys-Ser-Gln-Thr-Pro-Leu-Val-Thr-Leu-OH
  $R_f$=0.22.

$R_f$-values in Bu:Py:Ac:Wa (2:3/4:1/4:1) on SiO$_2$.

EXAMPLE XIII

H-Gly-Phe-Met(O)-Thr-Ser-Glu-Lys-Ser-Gln-Thr-Pro-Leu-Val-Thr-Leu-OH 225 mg Of the peptide obtained in Example I are dissolved in 20 ml of glacial acetic acid and 0.08 ml of 30% hydrogen peroxide is added. The mixture is stirred at room temperature for 1 hour. Then 300 mg of platinum black in glacial acetic acid are added to the mixture, which is stirred for 15 minutes in addition. The solid substance is filtered out and the filtrate is evaporated to dryness.

Yield 200 mg.

Through counter-current distribution chromatography in the solvent Bu:Ac:Wa (4:1:5) the peptide obtained is further purified. Yield 150 mg (as an acetate).

$R_f$ in Bu:Py:Ac:Wa (2:3/4:1/4:1)=0.19 on SiO$_2$.

EXAMPLE XIV

H-Gly-Phe-Met(O$_2$)-Thr-Ser-Glu-Lys-Ser-Gln-Thr-Pro-Leu-Val-Thr-Leu-OH 200 mg Of the peptide obtained in Example I are introduced into 5 ml of water to which are added in order of succession 0.025 ml of 0.5 M ammonium molybdate, 0.125 ml HClO$_4$, and 0.075 ml of 30% hydrogen peroxide. The mixture is stirred at room temperature for 4 hours, after which 5 ml of tertiary butanol/water (1:1) and ion exchanger in acetate form are added. After stirring for half an hour the ion exchanger is filtered out and the filtrate is evaporated to dryness. Yield 175 mg of peptide (in the form of an acetate).

R$_f$ in Bu:Py:Ac:Wa (2:3/4:1/4:1)=0.23 On SiO$_2$.

EXAMPLE XV

In the manner described in Example XIII the following peptides are prepared:
H-Met(O)-Thr-Ser-Glu-Lys-Ser-Gln-Thr-Pro-Leu-Val-Thr-Leu-OH
R$_f$=0.23.
desamino-Met(O)-Thr-Ser-Glu-Lys-Ser-Gln-Thr-Pro-Leu-Val-Thr-D-Leu-OH
R$_f$=0.32.
R$_f$ in Bu:Py:Ac:Wa (2:3/4:1/4:1) on SiO$_2$.

EXAMPLE XVI

In the manner described in Example XIV there are prepared:
H-Met(O$_2$)-Thr-Ser-Glu-Lys-Ser-Gln-Thr-Pro-Leu-Val-Thr-Leu-OH
R$_f$=0.27.
desamino-Met(O$_2$)-Thr-Ser-Glu-Lys-Ser-Gln-Thr-Pro-Leu-Val-Thr-Leu-OH
R$_f$=0.35.
D-Met(O$_2$)-Thr-Ser-Glu-Lys-Ser-Gln-Thr-Pro-Leu-Val-Thr-Leu-OH,
R$_f$=0.30.
Solvent system: Bu:Py:Ac:Wa (2:3/4:1/4:1) on SiO$_2$.

EXAMPLE XVII

Condensing Z-D-Ser-OH or Z-Leu-OH with the protected peptide H-Glu(OtBu)-Lys(Boc)-Ser-Gln-Thr-Pro-Leu-Val-Thr-Leu-OtBu in the manner described in Example IX yields the Z-protected undecapeptide. The latter peptide is hydrogenated followed by acid treatment in the manner described in Example V. 3. Obtained in this manner:
H-D-Ser-Glu-Lys-Ser-Gln-Thr-Pro-Leu-Val-Thr-Leu-OH
R$_f$=0.18.
H-Leu-Glu-Lys-Ser-Gln-Thr-Pro-Leu-Val-Thr-Leu-OH
R$_f$=0.22.
R$_f$ in Bu:Py:Ac:Wa (2:3/4:1/4:1) on SiO$_2$.

EXAMPLE XVIII

Condensing desamino-Ser-OH or 2,3-dihydroxypropionic acid with the protected peptide H-Glu(OtBu)-Lys(Boc)-Ser-Gln-Thr-Pro-Leu-Val-Thr-Leu-OtBu in the manner described in Example IX, followed by treatment of the resulting peptide with TFA as described in Example V. 3 yields the peptides:
desamino-Ser-Glu-Lys-Ser-Gln-Thr-Pro-Val-Thr-Leu-OH,
R$_f$=0,28.
2,3-dihydroxypropanoyl-Glu-Lys-Ser-Gln-Thr-Pro-Leu-Val-Thr-Leu-OH,
R$_f$=0,22.
R$_f$ in Bu:Py:Ac:Wa (2:3/4:1/4:1)

EXAMPLE XIX

In the manner described in Example IX. 1 the peptide:
H-Thr-Ser-Glu(OtBu)-Lys(Boc)-Ser-Gln-Thr-Pro-Leu-Val-Thr-Leu-OtBu, obtained as intermediate peptide in the process described in Example V. 3, is coupled either with 2-hydroxy-4-methylthio-butanoic acid or with 2-hydroxy-4-methyl-pentanoic acid. As described in Example I the resulting peptides are deprotected with TFA and further treated with ion-exchanger, yielding:
2-hydroxy-4-methylthio-butanoyl-Thr-Ser-Glu-Lys-Ser-Gln-Thr-Pro-Leu-Val-Thr-Leu-OH and
2-hydroxy-4-methyl-pentanoyl-Thr-Ser-Glu-Lys-Ser-Gln-Thr-Pro-Leu-Val-Thr-Leu-OH.

In the same manner the fragment H-Ser-Glu(OtBu)-Lys(Boc)-Ser-Gln-Thr-Pro-Leu-Val-Thr-Leu-OtBu, obtained as intermediate peptide in the process of Example X, is condensed with 2,3-dihydroxybutanoic acid. The resulting peptide is deprotected yielding:
2,3-dihydroxybutanoyl-Ser-Glu-Lys-Ser-Gln-Thr-Pro-Leu-Val-Thr-Leu-OtBu.

In the same manner the fragment H-Ser-Glu(OtBu)-Lys(Boc)-Ser-Gln-Thr-Pro-Leu-Val-Thr-Leu(OtBu) is condensed with N-methyl-threonine, followed by deprotection yielding:
H-Thr(N-CH$_3$)-Ser-Glu-Lys-Ser-Gln-Thr-Pro-Leu-Val-Thr-Leu-OH.

EXAMPLE XX

To 0.36 mmol. of the peptide H-Thr-Ser-Glu(OtBu)-Lys(Boc)-Ser-Gln-Thr-Pro-Leu-Val-Thr-Leu-OtBu (Ex. V. 3) in DMF is added 0.066 g p-nitrophenylacetate. The mixture is left to stand overnight, after which an additional equivalent (0.066 g) p-nitrophenylacetate is added. The mixture is stirred for one day, after which the solvent is evaporated. The residue is dissolved in DMF/MeOH (1:2) after which a fourfold quantity of ethylacetate is added. The precipitate obtained is filtered and washed with water. The protected N-acetyl derivative has a melting point of 210° C.;

R$_f$ on chloroform:methanol:water (70:30:5)=0.75 on SiO$_2$.

In the manner described before this protected peptide is deprotected with TFA and anisol and further treated with ion-exchanger in acetate form.

The peptide is further purified by counter current distribution, system Bu:Ac:Wa (4:1:5), and then lyophilized yielding:
Ac-Thr-Ser-Glu-Lys-Ser-Gln-Thr-Pro-Leu-Val-Thr-Leu-OH;

R$_f$ in Bu:Py:Ac:Wa (2:3/4:1/4:1)=0.29 on SiO$_2$.

EXAMPLE XXI 673 mg Of Boc-Thr-Ser-Glu(OtBu)-Lys(Boc)-Ser-Gln-Thr-Pro-Leu-Val-OH and 101 mg of HOBt (1.5 eq.) are dissolved in 10 ml of DMF and the solution was cooled to about −20° C. With stirring 193 mg H-Thr-α,β-dehydroleucine tert. butyl ester p-toluenesulphonate [obtained analogously to a procedure described in Tet. Letters 3609 (1975)] and 0.063 ml of N-ethylmorpholine are added, followed by 113 mg of DCCI (1.1 eq.). After stirring for 15 minutes at −20° C. and about 22 h. at room temperature, the precipitated DCHU is removed by filtration. Then the filtrate is concentrated and ethyl acetate is added. After cooling the precipitate formed is filtered, washed with ethyl acetate and ether and dried. Treatment of the protected dodecapeptide with TFA and purification of the resulting crude product is carried out as described before.

Yield: 245 mg.

$R_f$ in Bu:Py:Ac:Wa (2:3/4:1/4:1)=0.16 on $SiO_2$.

The same procedure as above is followed in the synthesis of

H-Thr-Ser-Glu-Lys-Ser-Gln-Thr-Pro-Leu-Val-Thr-2-hydroxy-4-methyl-pentanoic acid $R_f$=0.18 same solvent system.

We claim:

1. Peptide of the formula:

A-R-L-Ser-$R_1$-L-Thr-L-Pro-L-Leu-L-Val-L-Thr-B wherein
R represents the amino acid residue L-Lys or L-Arg,
$R_1$ represents the amino acid residue L-Glu or L-Gln,
B represents one of the following amino acid or peptide-radicals:
L-Leu-OH, (α-dehydro) Leu-OH
D-Leu-OH
L-Leu-L-Phe-OH
L-Leu-L-Phe-L-Lys-OH
L-MeLeu-OH
or the radical

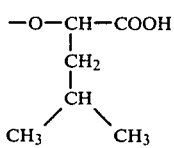

and A represents one of the following radicals or residues:
hydrogen
H-L-Glu
$Z_1$-L-Glu
$Z_2$-L-Ser-L-Glu-
H-$Q_1$-L-Thr-L-Ser-L-Glu-
$Q_2$-L-Thr-L-Ser-L-Glu-
$Z_3$-$Q_1$-L-Thr-L-Ser-L-Glu- or
$H_2N$-ALK-CO-L-Phe-$Q_1$-L-Ser-L-Glu-
in which
$Z_1$ represents H-L-Ser, H-D-Ser, desamino-Ser, 2,3-dihydroxy propanoyl or $H_2N$-ALK-CO-,
$Z_2$ represents H-L-Thr, H-D-Thr, desamino-Thr, 2,3-dihydroxybutanoyl or $H_2N$-ALK-CO;
$Q_1$ represents L-Met, L-Met (O), L-Met ($O_2$) or L-Leu
$Q_2$ represents H-D-Met, H-D-Met (O), H-D-Leu, H-D-Met ($O_2$), desamino MET, desamino Met (O), desamino Met ($O_2$), desamino Leu, 2-hydroxy-4-methylthiobutanoyl, 2-hydroxy-4-methylpentanoyl or the radical $H_2N$-ALK-CO,
$Z_3$ represents H-L-Phe, H-D-Phe, desamino Phe, 2-hydroxy-3-phenyl-propanoyl and $H_2N$-ALK-CO-,
and ALK represents an alkylene or alkylidene group with 1–6 carbon atoms,
as well as derivative thereof selected from acid addition salts, metal salts, aliphatic esters having from 1 to 18 carbon atoms in the alkanol moiety, unsubstituted amides, mono- or di-alkyl substituted amides, wherein the alkyl group contains from 1 to 6 carbon atoms, N-acyl derivatives wherein the acyl group contains from 1 to 6 carbons atoms, N-alkyl or N,N-dialkyl derivatives wherein the alkyl group has from 1 to 6 carbon atoms, and metal complexes.

2. A peptide according to claim 1 in which $R_1$ is L-Gln.

3. A peptide according to claim 1 in which R is L-Lys.

4. A peptide according to claim 1 in which B is L-Leu-OH.

5. Peptide according to claim 1 of the formula:

A-L-Lys
L-Ser-L-Gln-L-Thr-L-Pro-L-Leu-L-Val-L-Thr-L-Leu-OH, or a derivative thereof as defined in claim 1, in which A has the meanings indicated in claim 1.

6. Peptide according to claim 1, in which A represents one of the moieties:
$Z_2$-L-Ser-L-Glu
H-$Q_1$-L-Thr-L-Ser-L-Glu
$Q_2$-L-Thr-L-Ser-L-Glu or
$Z_3$-$Q_1$-L-Thr-L-Ser-L-Glu,
in whch $Z_2$, $Z_3$, $Q_1$ and $Q_2$ have the meanings indicated in claim 1.

7. Peptide according to claim 6, in which $Z_2$ represents: H-L-Thr or H-D-Thr.

8. A pharmaceutical composition containing as active ingredient, a psychopharmocological amount of a peptide of claim 1 in a pharmaceutically acceptable carrier.

9. A pharmaceutical composition according to claim 8 wherein the active ingredient is a psychopharmacological amount of the peptide of claim 7.

10. A pharmaceutical composition according to claim 8, wherein the dosage of the active ingredient is in the amount of from 1 μg to 1 mg per 1 kg body weight of the patient.

* * * * *